US009259208B2

(12) United States Patent
Nygaard et al.

(10) Patent No.: US 9,259,208 B2
(45) Date of Patent: Feb. 16, 2016

(54) ULTRASOUND PROBE

(75) Inventors: Per Ehrenreich Nygaard, Soborg (DK);
Gert Karlsson, Copenhgen NV (DK);
Bjorn Fortling, Helsinge (DK)

(73) Assignee: B-K Medical Aps, Herlev (DK)

( * ) Notice: Subject to any disclaimer, the term of this patent is extended or adjusted under 35 U.S.C. 154(b) by 1803 days.

(21) Appl. No.: 12/225,488

(22) PCT Filed: Mar. 23, 2007

(86) PCT No.: PCT/DK2007/000144
§ 371 (c)(1),
(2), (4) Date: Oct. 20, 2009

(87) PCT Pub. No.: WO2007/110077
PCT Pub. Date: Oct. 4, 2007

(65) Prior Publication Data
US 2010/0041996 A1    Feb. 18, 2010

Related U.S. Application Data

(60) Provisional application No. 60/785,373, filed on Mar. 24, 2006.

(51) Int. Cl.
*A61B 8/14*    (2006.01)
*A61B 8/00*    (2006.01)
(Continued)

(52) U.S. Cl.
CPC ............. *A61B 8/4488* (2013.01); *A61B 8/0833* (2013.01); *A61B 8/12* (2013.01); *A61B 8/145* (2013.01); *A61B 2017/3413* (2013.01); *A61B 2017/3447* (2013.01)

(58) Field of Classification Search
USPC ......... 600/407, 424, 437, 439, 440, 443, 444, 600/445, 446, 447, 459, 462, 463, 464, 466, 600/467, 461
See application file for complete search history.

(56) References Cited

U.S. PATENT DOCUMENTS 4,911,173 A    3/1990  Terwilliger
5,549,111 A *  8/1996  Wright et al. ................. 600/443
(Continued)

FOREIGN PATENT DOCUMENTS

EP    0 955 010 A1    11/1999
JP    02-071732       12/1990
(Continued)

OTHER PUBLICATIONS

International Search Report dated Dec. 5, 2007.
(Continued)

*Primary Examiner* — Tse Chen
*Assistant Examiner* — Jason Ip
(74) *Attorney, Agent, or Firm* — Anthony M. Del Zoppo, III; Driggs, Hogg, Daugherty & Del Zoppo Co., LPA

(57) ABSTRACT

An ultrasound probe for cavity scanning of a body, comprising: an elongated rod-like member (101), with a longitudinal axis (102), configured to accommodate at its one end a first transducer (104). The first transducer (104) has a field of view (105a, 105b) established by acquiring an image along radial scan lines in a first image plane that coincides with the longitudinal axis (102). The field of view covers more than 15 degrees of scan lines at each side of its intersection with the longitudinal axis and more than 15 degrees of scan lines at each side of its intersection with a transverse axis (103) that lies in the first image plane and is perpendicular to the longitudinal axis. The probe may comprise a first and second needle guide (203, 204) arranged to guide an instrument along a path (202, 201) which intersects with the first field of view (105), respectively.

17 Claims, 9 Drawing Sheets

(51) Int. Cl.
  *A61B 8/08* (2006.01)
  *A61B 8/12* (2006.01)
  *A61B 17/34* (2006.01)

(56) References Cited

U.S. PATENT DOCUMENTS

| | | | |
|---|---|---|---|
| 5,681,276 | A | 10/1997 | Lundquist |
| 5,681,277 | A | 10/1997 | Edwards et al. |
| 5,957,850 | A | 9/1999 | Marian, Jr. et al. |
| 6,045,508 | A | 4/2000 | Hossack et al. |
| 6,059,731 | A | 5/2000 | Seward et al. |
| 6,149,598 | A * | 11/2000 | Tanaka ............ 600/462 |
| 6,203,499 | B1 | 3/2001 | Imling et al. |
| 6,261,234 | B1 | 7/2001 | Lin |
| 6,285,898 | B1 * | 9/2001 | Ben-Haim ............ 600/374 |
| 6,433,902 | B1 | 8/2002 | Chiaroni et al. |
| 6,443,902 | B1 | 9/2002 | Sasady |
| 6,884,219 | B1 | 4/2005 | Pruter |
| 2004/0068191 | A1 | 4/2004 | Seward et al. |
| 2004/0152986 | A1 * | 8/2004 | Fidel et al. ............ 600/459 |
| 2006/0036176 | A1 | 2/2006 | Angelsen et al. |

FOREIGN PATENT DOCUMENTS

| | | |
|---|---|---|
| WO | WO 94/13208 | 6/1994 |
| WO | WO 96/10958 | 4/1996 |
| WO | WO 98/38486 A | 9/1998 |
| WO | WO-9934735 | 7/1999 |
| WO | WO-00/19906 | 4/2000 |

OTHER PUBLICATIONS

International Search Report for International Application No. PCT/DK2007/000142, mailed Feb. 8, 2007 (2 pages).

International Search Report for International Application No. PCT/DK2007/000144, dated May 12, 2007 (3 pages).

* cited by examiner

ULTRASOUND PROBE

CROSS-REFERENCE TO RELATED APPLICATIONS

This application is a national phase application of international Application No. PCT/DK2007/000144, filed Mar. 23, 2007, and claims the benefit of U.S. Provisional Application No. 60/785,373, filed Mar. 24, 2006, the content of both of which is incorporated herein by reference.

BACKGROUND

Various ultrasound techniques and devices have been developed for imaging the interior of a body e.g. the human body. One application of ultrasound imaging has been in the medical field, and in particular, in endocavitary probes (e.g., biopsy guidance endocavitary probes). Such probes may be used, for example, for endovaginal examination (e.g., to examine the uterus, ovaries, etc.), endorectal examination (e.g., to examine the rectal wall, prostate, etc.), and/or other medically-related applications. It should be noted that for instance endorectal examination is rather unpleasant and that biopsy taking is rather painful and therefore typically requires local anaesthesia. Typically, endocavitary probes include a linear array transducer positioned at the distal end or front end of the probe that is to be inserted into a cavity of a body. The transducer provides an imaging plane for viewing structures/features of the body and/or another instrument (e.g., a biopsy needle) that, for example, may be guided into the body via the probe. The imaging plane may be provided at a side of a probe (corresponding to a "side-fire" transducer) or the front of the probe (corresponding to an "end-fire" transducer).

Endocavitary probes typically have an elongated rod-like shape configured with a handle that extends as a portion of the elongated rod-like shape, but in the end opposite the distal end. Other ultrasound probes are, contrary to endocavitary probes, configured for placing the probe on the skin of the body to provide imaging of the interior of the body located beneath the skin. Still other probes (e.g. intra-operative probes) are configured for placing the probe directly on organs inside the body during surgery operations.

Ultrasound probes are, during use as a probe for imaging purposes, connected to an image processor e.g. in the form of a special purpose computer. The image processor is configured to provide stimulation signals to the probe for emission of ultrasound pulses and to record reflected ultrasound signals in response thereto. Recorded ultrasound signals are processed to provide a presentation of the reflected ultrasound signals in the form of an ultrasound image on a display screen e.g. a computer monitor.

Use of an ultrasound probe for imaging purposes is also denoted ultrasound scanning or simply scanning. Scanning is commonly understood as the act of systematically emitting a (finely focused) beam of e.g. ultrasound into a medium at different locations across the medium in order to produce an image of structures contained in the medium. The beams are emitted systematically e.g. by transducer elements arranged in a linear or curved linear transducer array. An image is generated from reflections received in response to emitted ultrasound beams.

The transducer(s) of the probe has/have a so-called field of view which is the sector (usually with a shape like a sector of a circle) from which reflections are recorded and displayed as an image. The field of view is also denoted the imaging plane since field of view can be thought of as a very thin sector of a disc. A very thin sector is desired in order to provide precise spatial location (e.g. of organs or tumours). This is provided by focusing the emitted ultrasound waves in a direction transverse to the linear array. Thus, the sector can be described as a plane or sector of a circle, but it will have a certain thickness. The width of the field of view is determined by the length of the linear array and the shape of the array. Typically, the array is shaped to extend along an arc or a circle. The depth of the field of view is among other things determined by the length of a time-window within which reflected ultrasound signals are recorded.

The focusing required to obtain the desired field of view in a direction transverse to the length of the array is typically obtained by giving each of the transducer elements a concave surface shape (in a direction transverse to the length of the array). It is also desired to have a fine focusing in the image plane i.e. in a direction along the length of the array. This is typically achieved by giving each of the transducer elements a flat surface shape (in a direction transverse to the length of the array) and then obtaining a desired focusing electronically. The focused image acquired from the field of view comprises a number of radial lines. The number of radial lines in the image corresponds to radial scan lines (in the tissue scanned) along which focusing is provided. Thus, the field of view comprises a number of scan lines.

The probe typically provides either signals from a single transducer array for display as one image or rather sequence of images representing the ultrasound imaging from the field of view of the single transducer array. Some ultrasound probes comprise two arrays arranged perpendicular to each other to provide bi-plane imaging that is two separate images acquired from the two different arrays. Thereby a so-called sagittal image plane and transverse image plane can be provided for simultaneous display. Bi-plane imaging provides more spatial information due to acquisition of two images from two transducers with different fields of view.

For the vast majority of uses of endocavitary probes, the probe is used to monitor the safe guidance of an instrument e.g. a biopsy needle. This monitoring is typically carried out by means of a probe configured with a guide that guides the instrument along a predefined path. The transducer(s) of the probe and the guide are mutually arranged so as to remain in a fixed position relative to each other and so as to obtain a field of view which covers at least a portion of the predefined path along which the instrument is guided. Thereby safe guidance of an instrument can be obtained.

The above described observations and techniques are well-known in the field of ultrasound probes. Below, reference is made to different endocavitary probes.

RELATED PRIOR ART

JP 02071732-A discloses an elongated ultrasound probe for biplane ultrasound imaging of a prostate. The elongated probe comprises an end portion with a longitudinally arranged transducer array for sagittal imaging and a transversely arranged transducer array for transverse imaging, where the longitudinally arranged array is placed perpendicular to the transversely arranged array, but on the more distal end of the end portion, such that the image planes of the two transducers intersect orthogonally. The arrays are formed in a convex arc shape so as to provide the image planes from radial scan lines. The arc shapes have a relatively smooth shape.

The ultrasound probe is disclosed interconnected with a biopsy needle guide configured for guiding a biopsy needle longitudinally to the elongated ultrasound probe, but offset a certain distance from the probe. The biopsy needle guide is configured such that the biopsy needle is guided through the opening of the body cavity and penetrates the body from the interior of the body cavity.

U.S. Pat. No. 6,443,902-B1 discloses an ultrasound probe with a detachable needle guide for collecting tissue samples. The ultrasound probe is configured for insertion into a body cavity and comprises two transducer arrays and a needle guide assembly for guiding a biopsy needle. The transducer arrays are arranged perpendicular to each other as described above, so as to provide bi-plane imaging.

The needle guide assembly is separate from, but can be interconnected with the ultrasound probe. The ultrasound probe can be covered by a soft sheath and the needle guide assembly can then be attached to the probe, but such that the sheath prevents contact between the probe and assembly. Thus, the needle guide is arranged outside the sheath in such a manner that a needle of the needle guide need not penetrate the sheath. Thereby, only the assembly, but not the probe needs sterilization after use. The needle guide is arranged to guide the needle in a direction transverse to a longitudinal axis of the elongated ultrasound probe. The biopsy needle guide is configured such that the biopsy needle is guided through the opening of the body cavity and penetrates the body from the interior of the body cavity.

U.S. Pat. No. 6,261,234-B1 discloses a probe for providing simultaneous viewing of an instrument in two ultrasound imaging planes (biplane instrument guidance). The probe is configured as an elongated member with an end-portion that is configured to accommodate two transducer arrays. The two transducer arrays are in the form of a side-fire transducer array and end-fire transducer array arranged along a respective convex arc shape to provide two imaging planes. The two imaging planes intersect at a line which coincides with an instrument path. A needle guide in the form of a groove of the probe is arranged to guide the needle along the instrument path when it protracts from the groove. Seen towards the end-portion, the transducer arrays are arranged in an L-shaped configuration, where the groove has an opening, wherefrom the needle protracts, at the corner of the L-shape.

Despite the above prior art documents disclose important improvements, the cited prior art documents do not fully take advantage of the possibilities related to patient comfort and effectiveness/efficiency in medical diagnosis situations.

SUMMARY OF THE INVENTION

There is provided an ultrasound probe for cavity scanning of a body, comprising: an elongated member, with a longitudinal axis and an end-portion, configured to accommodate a first transducer; a second transducer configured to provide a second image plane transverse to a longitudinal axis of the elongated member. The first transducer has a field of view established by acquiring an image along radial scan lines in a first image plane that coincides with the longitudinal axis. The field of view covers more than 15 degrees of scan lines at each side of its intersection with the longitudinal axis and more than 15 degrees of scan lines at each side of its intersection with a transverse axis that lies in the first image plane and is perpendicular to the longitudinal axis.

Consequently, the probe can be used for two different scanning principles in a sagittal imaging plane: end-fire scanning and side-fire scanning. This greatly increases the use of the probe since each of the scanning principles has its own advantages. Since the one and same probe can be used for the two different scanning principles the operator of the probe can use the same probe for both types of scans. The operator does not have to switch between two different probes. Thereby, the patient will be exposed to a less complicated endocavitary examination and patient discomfort is thus reduced. Further, due to the less complicated endocavitary examination, effectiveness and efficiency in medical examination situations is greatly increased.

The second transducer array provides a field of view in a second image plane transverse to the longitudinal axis of the elongated member. This greatly improves the spatial imaging capability in that the second imaging plane extends in an additional (third) dimension than the two dimensions of the first imaging plane. This bi-plane imaging capability is expediently used for providing image data from the second transducer and a portion of the first transducer covering a sector about the transverse axis.

The probe also provides improvements relating to instrument guidance. When the probe is used in combination with instrument guidance, the two scanning principles mentioned above allow biopsy to be taken and monitored along two differently located paths while the probe remains in the body cavity. The two different paths will extend through different locations of the body and thus provide for taking monitored biopsies at more locations in the same cycle of operations i.e. the cycle of operations where the probe is and remains inserted in the. body cavity.

Expediently, the first transducer and/or second transducer have/has a field of view which are/is centred about the longitudinal axis and/or transverse axis, respectively. Thereby, the field of view provided by the probe is more intuitively arranged about zero degrees and/or ninety degrees with respect to the longitudinal axis of the often rod-shaped probe.

The field of view, at each side of its intersection with the longitudinal axis or transverse axis, preferably covers a radial section larger than an angle selected from the group of 20, 25, 30, 35, 40, 45, 50 and 55 degrees. The maximum size of the angular coverage of the field of view is determined by the shape and length of the transducer array. But the size of the field of view providing image data can be reduced electronically as desired. For larger radial sections about the longitudinal and transverse axis the radial sections may overlap.

When the field of view established about the longitudinal axis and the field of view established about the transverse axis are of substantially same size, the respectively acquired images can expediently occupy the same field on a display screen. Thereby switching between the two images intuitively causes less confusion.

In a preferred embodiment, the first transducer comprises a curved array shaped to substantially follow an arc segment of a circle a with a radius selected form the ranges 2 to 20 millimetres and/or 4 to 16 millimetres and/or 4 to 12 millimetres and/or 6 to 12 millimetres. Thereby imaging comprising 5 non-phase array processing can be performed while providing a sufficiently broad field of view. Likewise, the second transducer can comprise a curved array shaped to substantially follow an arc segment of a circle a with a radius selected form the ranges 2 to 20 millimetres and/or 4 to 16 millimetres and/or 4 to 12 millimetres and/or 6 to 12 millimetres. When both the first transducer and the second transducer comprise a curved array shaped to substantially follow arc segments of circles with substantial same radius, the images acquired by the transducers can be presented in a like layout.

Expediently, the second transducer array is inclined to provide the second image plane at an angle less than 90 degrees with respect to the longitudinal axis towards the one end of the elongated member. Thereby, a sector of the first image plane about the transverse axis and the second image plane can be arranged to coincide. Thereby, e.g. an instrument can be located in both image planes to provide improved spatial location.

Preferably, the second transducer is inclined to provide the first image plane at an angle that is within the range of 40 to 110 degrees with respect to the longitudinal axis towards the one end of the elongated member. An inclination of about 70-80 degrees e.g. 85 degrees has been found to be especially expedient.

The first transducer is expediently arranged on the more distal portion of the end than the second transducer array. Thereby, the first transducer can provide end-fire imaging without the end-fire field of view colliding with the structure of the second transducer.

In an embodiment the ultrasound transducer is configured to enable selection of: a first mode wherein an end-view image is acquired from a first portion of the first transducer array with a field of view that covers scan lines at each side of the longitudinal axis, and a second mode wherein a side-view image is acquired from a second portion of the first transducer array with a field of view that covers scan lines at each side of the transverse axis. The first and second portions of the first transducer array have a field of view that covers a first and a second sector of ray scan lines; and where the first and second sectors are arranged to cover a common sector of scan lines. Thereby the first transducer is utilized more efficiently in that the elements of the first transducer, which form the common or overlapping sectors, are used in both images corresponding to both sectors. Consequently, the same transducer line array can be used for acquiring both images.

When a transverse image additionally is acquired in the second mode, but from the second transducer array, two different and acknowledged principles for scanning of prostate are provided: bi-plane scanning in the second mode and end-fire scanning in the first mode. The bi-plane scanning comprises the side-fire scanning and the scanning in the transverse imaging plane.

When the first transducer array covers a sector of say more than 160 degrees, more transducer elements of the line array than pins of a sensible electrical connector will typically be present. Thus, on the one hand pure parallel read-out of the individual transducer elements is ruled out. On the other hand, very few pins would not provide for read-out of all the transducer elements within a sensible timeframe. Therefore, the probe is conveniently configured with a multiplexer for a combined parallel and time-multiplexed output of image data.

Preferably, the probe is configured with coupling means for interconnection with a biopsy assembly with complementary coupling means. Thereby, the probe can be separately protected by a cover to avoid sterilization of the probe between each and every use of the probe. The coupling means and the probe and the biopsy assembly shall allow sufficient clearance for the cover to protect the probe without being punctured or flawed.

The probe or biopsy assembly may comprise a first needle guide configured to guide a needle along a path which intersects with the first field of view; and a second needle guide configured to guide a needle along a path which intersects with the first field of view and the transverse axis. Thereby, the instrument (e.g. a needle) can be guided safely since it can be monitored along its path.

A known configuration comprises a biopsy needle guide for guiding a needle a long a path longitudinal to, but offset from a rod-shaped probe and a side-fire monitoring of the path (cf. U.S. Pat. No. 6,443,902-B1, FIG. 1). However, this configuration poses problems when used for taking biopsies of a prostate. A biopsy regimen can include e.g., at least two biopsies from the apical area of the prostate (closest to the pelvic floor muscles). In this situation the biopsy needle will first penetrate into the human tissue at a small, but sometimes significant distance behind the sagittal image projection which projects from the first transducer. Examining the anatomy slightly below the apex more closely identifies the different pelvic floor muscles. It is then clear that any attempt to introduce a biopsy needle along, but offset from the probe will cause the needle to come close to—or even pass through parts of the muscles.

Therefore, expediently, the first needle guide is arranged to guide a needle in a direction transverse to the longitudinal axis, and the second needle guide is arranged to guide the needle in a direction along the elongated member.

The transversely guided biopsy needle is thus guided through the opening of the body cavity and penetrates the body from the interior of the body cavity. Thereby, the basal area (opposite the apical area) of the prostate can be sampled by biopsy while being safely monitored by the side-fire imaging. The longitudinally guided biopsy needle is also guided through the opening of the body cavity (very close to the periphery of the probe) and penetrates the body from the interior of the body cavity. Likewise, but when rotated about 90 degrees and introduced into the body at a more steep angle, the apical area of the prostate can be sampled by biopsy while being safely monitored by end-fire imaging. Thereby, the prostate apex and basal can be sampled by biopsy in the same cycle of operation while being safely monitored by either side-fire or end-fire imaging.

The combination of the transversely guided biopsy needle and longitudinally guided biopsy needle provides a superior probe for taking biopsies of a prostate in a single cycle of operations.

Preferably, the first needle guide is arranged to provide an angle between the needle, when inserted into the needle guide, and the longitudinal axis of the elongated member within the range of 10 to 50 degrees. The needle guide can be shaped as a substantially straight tube or curved tube.

Preferably, the first needle guide provides an angle of a needle, when inserted into the first needle guide, at its projection from the first needle guide and the longitudinal axis of the elongated member within the range of 10 to 50 degrees. The projection of the needle can be controlled by the needle guide to obtain the desired angle of protraction.

Expediently, the needle guides are arranged, with respect to the elongated member, to make the needles, when inserted into the needle guides, protract at opposite positions with respect to a cross-section of the biopsy assembly. Thereby, the relevant locations for taking samples of the tissue under examination can be addressed by the paths of the biopsy needles by firstly using the first needle guide to take first biopsies (removing the biopsy needle) and then simply rotating the probe to take second biopsies. This is far more convenient than actually changing probe.

In a preferred embodiment, the second needle guide extends along the periphery of the elongated member, but offset from the periphery in a direction away from the point of gravity in a cross-sectional view of the elongated member.

In a preferred embodiment, the elongated member has a shape that is configured for mechanical interconnection with a probe and to match a recess of a probe so as to provide a combination of the assembly and probe, when interconnected, that can be circumscribed by a cylinder that covers at least a portion of the length of the elongated member and has a diameter that is within the range of 12 to 30 millimetres.

The needle guides may be shaped as a tube with an entry end configured for entry of a needle and an exit end configured for the needle to project from the needle guide. The smooth shape of a tube has a smaller tendency to collect dirt and remainders of tissue, since there are fewer protrusions.

To reduce the risk of confusing the acquired images, marking on biopsy needle guides may correspond to marking of acquired bi-plane images, respectively, when displayed on a display screen.

BRIEF DESCRIPTION OF THE DRAWINGS

Preferred embodiments will be described in greater detail and with reference to the drawing in which.

DESCRIPTION OF A PREFERRED EMBODIMENT

Figure 1:
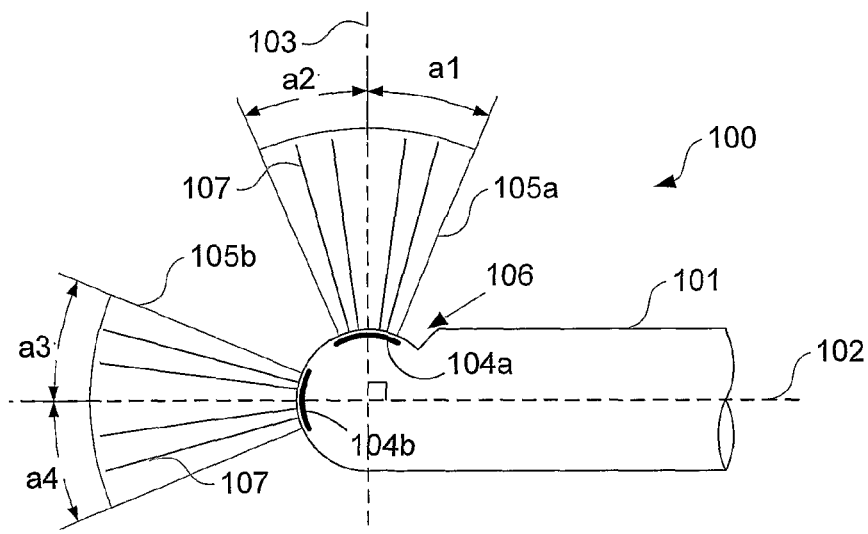
FIG. 1 shows a cross-sectional view of an ultrasound probe comprising a transducer array with a field of view.

FIG. 1 shows a cross-sectional view of an ultrasound probe comprising a transducer array with a field of view. The ultrasound probe 100 is configured for cavity scanning of a body in that it has an elongated or rod-like shape which can be introduced into the cavity. In general such an ultrasound probe has a handle, a shaft and a distal end configured to accommodate an ultrasound transducer 104a; 104b. Only the portion of the shaft towards the distal end is shown—the handle is not shown. The distal end of the probe may also be denoted a scanning head or the scanning end of the probe. The probe or rather the distal end of it may also be seen as a housing in that it accommodates transducer array. In general the probe has the shape of an elongated member.

A longitudinal axis 102 of the probe or elongated member is shown as a dashed line. A transverse axis 103 perpendicular to the longitudinal axis 102 is also shown as a dashed line.

In one aspect, the probe 100 is configured to accommodate at its distal end a first transducer in the form of two detached arrays 104a;104b of ultrasound transducer elements. The two arrays 104a;104b are arranged in extension of one another, but at an offset distance in the direction of extension. However, the offset distance may be so small that the arrays provide imaging corresponding to a single array. In another aspect, as described further below, the first transducer is in the form of a single array. The arrays or array provide(s) an imaging plane coinciding with the longitudinal axis 102 and transverse axis 103 i.e. the axes lies in the imaging plane. For medical uses, this imaging plane is also denoted a sagittal imaging plane.

The transducer arrays 104a,104b are shaped so as to provide a desired field of view in the sagittal imaging plane. It is in general desired to use small (i.e. short) arrays. Consequently, the arrays are shaped along a convex arc shape to emit and receive ultrasound wave energy along radial scan lines. The radial structure of the scan lines provides a sector of a circle which becomes broader with the distance to the transducer. The smaller the radius of the convex arc shape, the broader the sector of the circle. The above is based on a circular arc shape. However, other arc shapes that provide radial scan lines can be used. Such other arc shapes can comprise sections of straight linear arrays each comprising a number of transducer elements. Complex arc shapes comprising sections with different radiuses can also be applied to obtain a desired field of view.

Since in general small clearance or close contact between the transducer and the housing of the distal end is desired, the shape of the transducer dictates the shape of the housing about the transducer. In the shown configuration, the housing and the transducer has the shape of a portion of a circular arc. Since it is an objective to provide a design of the probe which is suitable for cavity scanning and thus for suitable for being introduced into the cavity, the probe has a depression 106 behind the housing that accommodates the transducer arrays 104a,104b. Thereby the field of view 105a about the transverse axis 103 is allowed to extend further towards the handle end of the probe without requiring a larger diameter of the housing. The arrays 104a and 104b of the first transducer provide partial fields of view 105a and 105b, respectively. The field of view 105a,105b provided by the first transducer 104a,104b covers more than 15 degrees of scan lines at each side of its intersection with the longitudinal axis 102 and more than 15 degrees of scan lines at each side of its intersection with a transverse axis 103. Thus angles a1, a2, a3 and a4 are larger than 15 degrees. The angles need not be equal. In a preferred embodiments a1 plus a2 is approximately equal to a3 plus a4.

For most practical purposes a partial field of view of more than 30 degrees is desired. Thus, preferably, the field of view, at each side of its intersection with the longitudinal axis or transverse axis, covers a radial section larger than an angle selected from the group of 20, 25, 30, 35, 40, 45, 50 and 55 degrees.

It is shown that the first transducer has partial fields of view which are centred about the longitudinal axis 102 and the transverse axis 103. It is also shown that the field of view 105b established about the longitudinal axis 102 and the field of view 105b established about the transverse axis 103 are of substantially same size.

Figure 2:
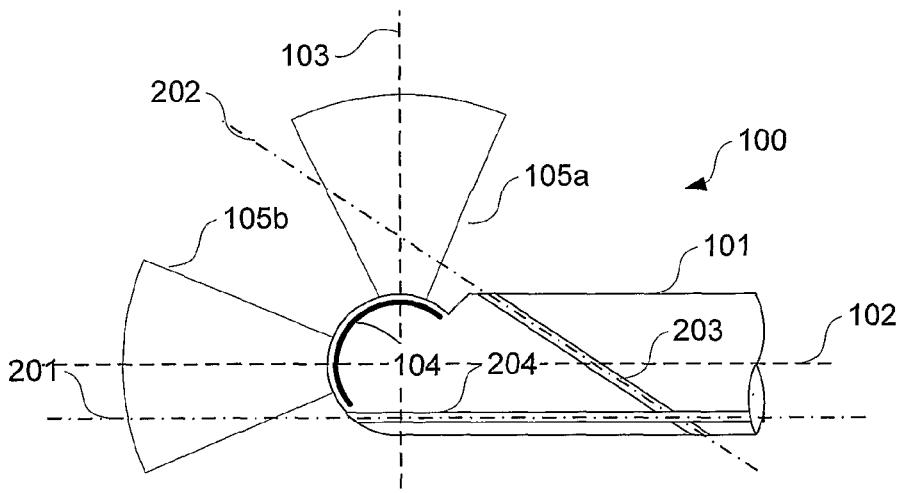
FIG. 2 shows a cross-sectional view of an ultrasound probe comprising a needle guide arranged longitudinally and a needle guide arranged transversely.

FIG. 2 shows a cross-sectional view of an ultrasound probe comprising a needle guide arranged longitudinally and a needle guide arranged transversely. This arrangement of the needle guides enhances the use of the ultrasound probe to be used for taking biopsy samples along two different. biopsy paths while providing safe monitoring of both the paths.

The transverse needle guide 203 and longitudinal needle guide 204 can, as shown, be integrated with the probe body 101. Alternatively, as described further below, the probe can be configured with coupling means for interconnection with a biopsy assembly with complementary coupling means.

The probe body 101 comprises a first, transverse needle guide 203 configured to guide a needle along a path 202 which intersects with the field of view 105a established about the transverse axis 103. It further comprises a second, longitudinal needle guide 204 configured to guide a needle along a path 201 which intersects with the field of view 105b established about the longitudinal axis 102. Thereby, a needle or other instrument guided, by means of the needle guide, along one of the paths will intersect with at least some of the scan lines of the respective fields of view and thus be viewable during the ultrasound scanning. Thereby safe monitoring of both the paths is provided.

The transverse needle guide 203 guides a needle along the path 202. This path intersects the scan lines of the field of view 1 05a established about the transverse axis 103 at angles say between about 25 to 90 degrees. Thereby, the path 202 is viewable across the entire field of view.

The transverse needle guide is arranged to provide an angle between the needle, when inserted into the needle guide, and the longitudinal axis of the elongated member within the range of 10 to 50 degrees, preferably at about 15 to 20 degrees, e.g. at 17 degrees.

For a straight transverse needle guide the same angle is provided along the entire path 202. But a needle guide configured to provide a curved path can also be employed. Such a curved guide can provide an angle of a needle, when inserted into the first needle guide, at its projection from the first needle guide and the longitudinal axis of the elongated member within the range of 10 to 50 degrees.

The longitudinal needle guide 204 guides a needle along the path 201. This path intersects the scan lines of the field of view 105b established about the longitudinal axis 102 at angles say between about 5 to 25 degrees. Thereby, the path 201 is viewable only at a partial sector of the field of view.

Seen along the longitudinal axis 102 at a point more distal than the housing of the probe and towards the housing of the probe, the needle guides are arranged, with respect to the elongated member, to make the needles, when inserted into the needle guides, protract at opposite positions with respect to a cross-section of the biopsy assembly. Thus, e.g. a prostate can be addressed by either one of the paths 201,202 by rotating the probe 180 degrees about its longitudinal axis.

In this embodiment, the first transducer is configured as a single array 104. Thereby, the signals to and from the elements of the transducer array can be elected electronically so as to provide differently sized or positioned images from the transducer array. This will be explained in greater detail further below.

Figure 3:
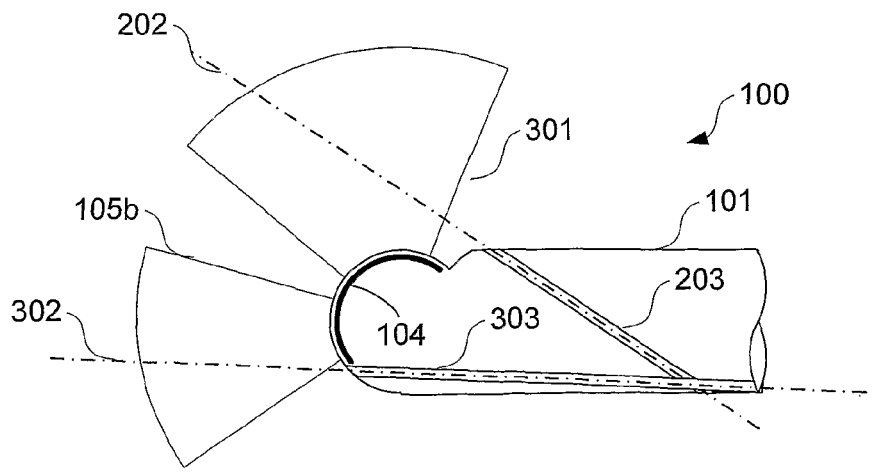
FIG. 3 shows a cross-sectional view of an ultrasound probe comprising a needle guide arranged along the ultrasound transducer, but inclined.

FIG. 3 shows a cross-sectional view of an ultrasound probe comprising a needle guide arranged along the ultrasound transducer, but inclined. In this embodiment, one of the needle guides 303 extend in a direction along the elongated member 101. This direction may be parallel to a longitudinal axis of the elongated probe or, as shown, inclined with respect to a longitudinal axis of the elongated probe. This inclination is preferably arranged such that the path 302 crosses the longitudinal axis in front of the transducer 104. The needle guide 303 can be configured as a straight channel or a curved channel. Thus, the inclination need not be present—or be the same—along the entire length of the guide 303.

Figure 4:
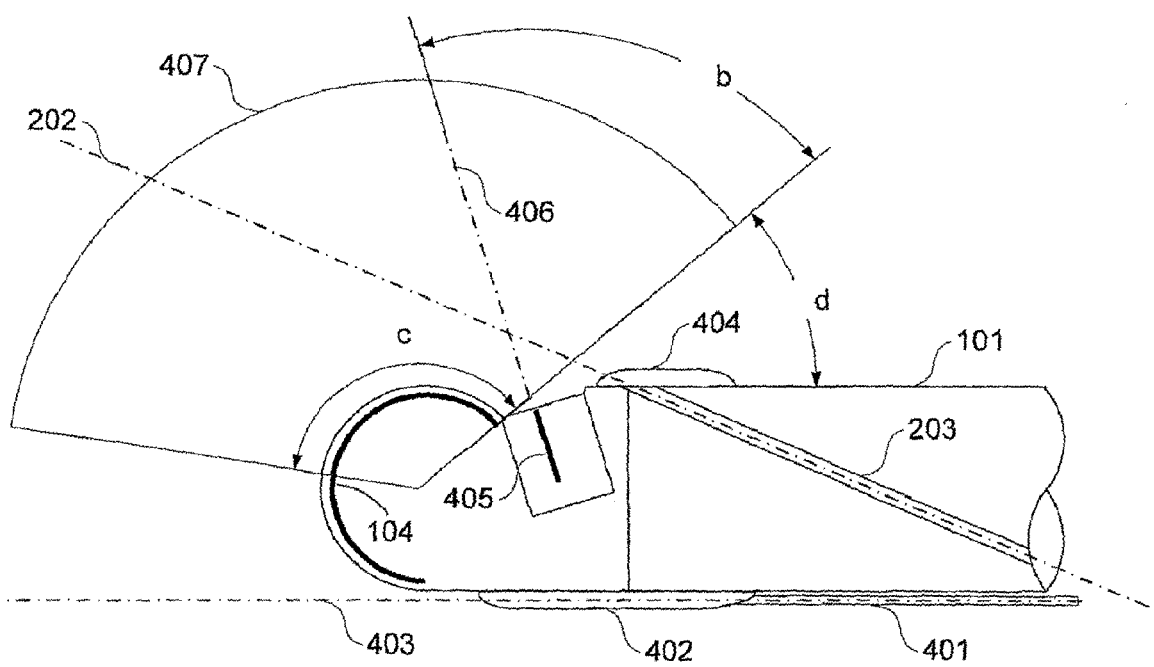
FIG. 4 shows a cross-sectional view of an ultrasound probe in a mode providing sagittal side-fire imaging and a transverse imaging.

FIG. 4 shows a cross-sectional view of an ultrasound probe in a mode providing bi-plane imaging. The bi-plane imaging is provided by sagittal side-fire imaging and transverse imaging. The transverse imaging is provided by a second transducer array 405 to provide a second image plane 406 transverse to the longitudinal axis of the elongated member. Preferably, the second image plane 406 is orthogonal to the first image plane 407. The second image plane is also denoted the transverse image plane.

The transverse image plane 406 may be arranged so as to coincide with the axis 103 transverse (perpendicular) to the longitudinal axis 102 i.e. at right angles or about right angles. However, as shown, it is preferred that the second transducer array is inclined to provide the transverse image plane at an angle of less than 90 degrees with respect to the longitudinal axis towards the distal end of the elongated member. The transverse image plane 406 is shown at an angle of about (180 degrees minus 107 degrees equal to) 73 degrees relative to the longitudinal axis 102. Preferably, the second transducer is inclined to provide the second image plane at an angle that is within the range of 40 to 85 degrees with respect to the longitudinal axis towards the one end of the elongated member.

As the second transducer 405 is arranged in an inclined position close to the first transducer 104, the image plane 406 provided by the second transducer intersects the field of view provided by the first transducer. Thereby, since some spatial locations appear in both imaging planes, the ability provided by the second imaging plane 406 to scan outside the sagittal imaging plane 407 can improve spatial location determination. As it can be seen, the transverse field of view will intersect only scan lines of a sector the first field of view i.e. a partial sector of the first field of view.

As it is shown, the first transducer 104 is arranged at the one end of the elongated member 101, but on the more distal portion of the end than the second transducer array 405.

It is also shown that only a portion (i.e. a 131.7 degrees sector closest to the transverse array 405) of the first transducer 104 is used for providing the sagittal field of view i.e. the portion enclosed by the depicted field of view 407. The remaining portion of the first transducer 104 may or may not be used when the probe is in a mode where bi-plane imaging is provided.

In this embodiment the transverse needle guide comprises a channel 203 which extends at its distal end into a projection 404. The longitudinal needle guide comprises a channel 401 which extends at its distal end into a projection 402. An instrument, e.g. needle, follows the path 403.

Preferably, the distal opening of the channel 203 is located relative to the (left side boundary of the) field of view 407. Thereby, the path 202 can be monitored/scanned when the needle starts to protract from the opening of the channel 203 and potentially could damage tissue or organs of a body.

The angle b designates the inclination of the transverse field of view 406 relative to the left boundary of the (sagittal) image plane (407). The angle c designates the coverage of the (sagittal) field of view 407. The angle d designates the angle between the longitudinal axis and the left boundary of the (sagittal) image plane (407).

Figure 5:
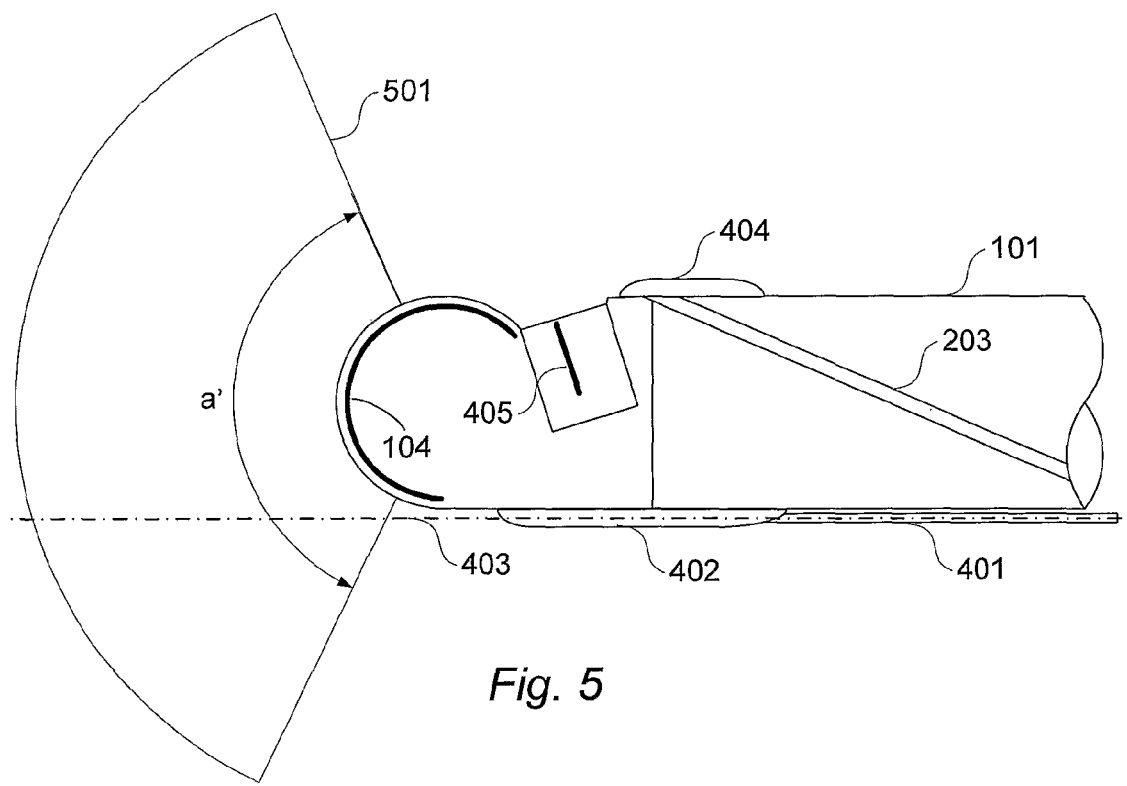
FIG. 5 shows a cross-sectional view of an ultrasound probe in a mode providing sagittal end-fire imaging.

FIG. 5 shows a cross-sectional view of an ultrasound probe in a mode providing sagittal end-fire imaging. In this mode another portion of the first transducer array is used for acquiring the image (image signals). The end-fire image is provided from a field of view corresponding to a sector of a circle of about 140 degrees. The field of view 501 is substantially centred about a longitudinal axis 102 of the probe 101. However, this centring may deviate about ±4 degrees as the elements of the array may be located such that perfect centring is inconvenient. The angle e designates the coverage of the sagittal end-fire view 501.

The probe can be operated in one of two modes: one mode providing side fire imaging or bi-plane imaging comprising side-fire imaging and another mode providing end-fire imaging. Preferably the probe is configured to enable selection of a first mode wherein an end-view image is acquired from a first portion of the first transducer array with a field of view that covers scan lines at each side of the longitudinal axis. It is possible to shift to a second mode wherein a side-view image is acquired from a second portion of the first transducer array with a field of view that covers scan lines at each side of the transverse axis. In the second mode the transverse image is also acquired. The modes can be selected either by operating one or more buttons on the probe or at the image-processor console.

Figure 6:
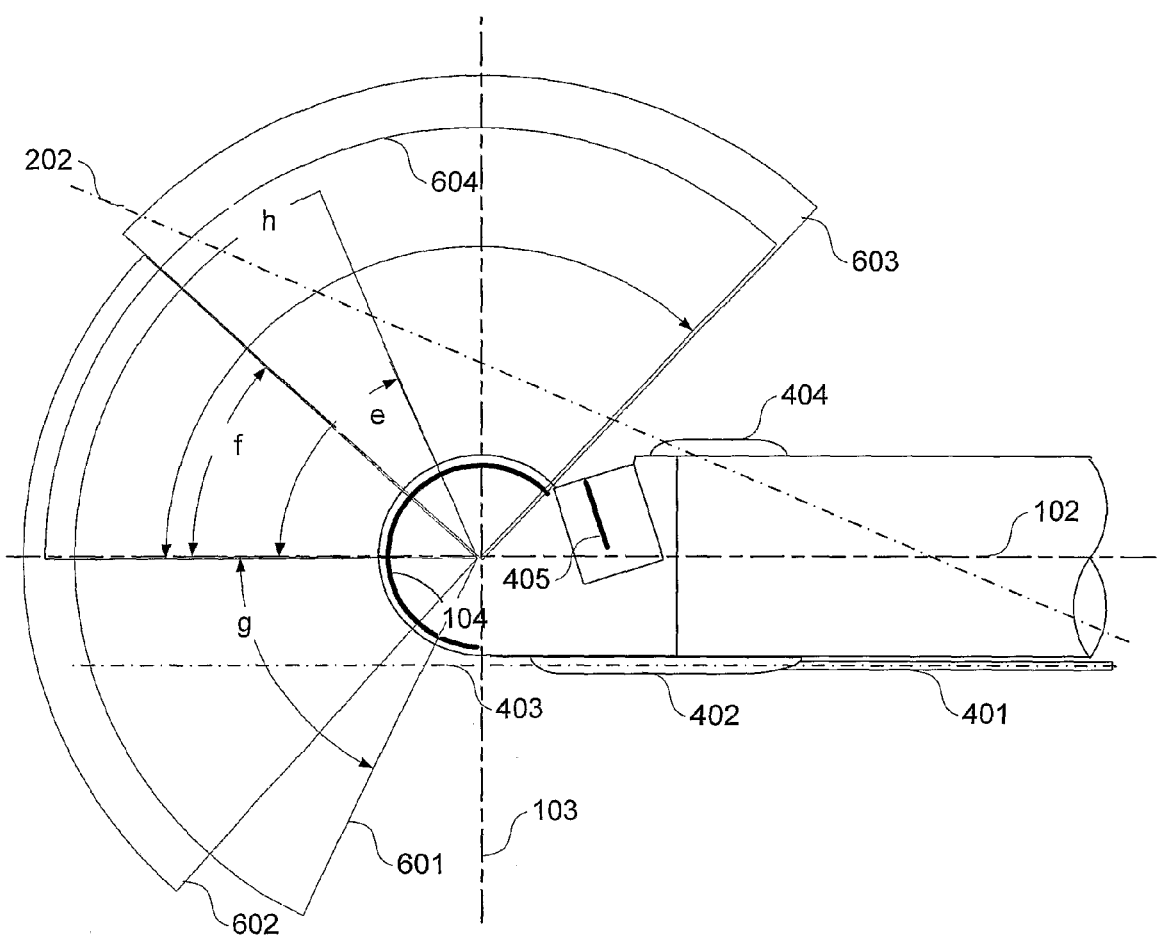
FIG. 6 shows a cross-sectional view of an ultrasound probe shown with different field of views.

FIG. 6 shows a cross-sectional view of an ultrasound transducer shown with different field of views. Four different fields of views in the sagittal image plane obtainable by the first transducer is shown. Two end-fire fields of views and two side-fire fields of views are shown.

A first end-fire view 601 has a broader angular coverage than a second end-fire view 602. The first end-fire view 601 covers a circular section of about 132 degrees. The second end-fire view 602 covers a circular section of about 84 degrees.

A first side-fire view 604 has a broader angular coverage than a second side-fire view 603. The first side-fire view 604 covers a circular section of about 90 degrees. The second end-fire view 602 covers a circular section of about 132 degrees.

The second end-fire view 602 and the second side-fire view 603 are positioned next to each other and have in combination a non-overlapping coverage. If these side-fire and end-fire views are the desired views for all uses of the probe, the first array 104 need not cover a larger field of view. However, these side-fire and end-fire views may also represent electronically selected field of views from the—larger—field of view provided by the first transducer.

The first end-fire view 601 and the first side-fire view 604 are positioned such that they establish a common field of view or overlap. This may be desired in any event since the common field of view improves the ability to keep a reference location when switching from the side-view to the end-view and vice versa. However, this may also be so since the field of view provided by the first transducer array has a limited length. Thus, the fields of view (or sectors) are arranged to cover a common sector of scan lines.

The angle f designates the angle between the longitudinal axis and the left side boundary of the (sagittal) field of view 603 and the angle g designates the angle between the longitudinal axis and the left side of view 601. Angle h designates the coverage of view 601.

The probe will typically comprise electronic circuitry configured with a multiplexer for a combined parallel and time-multiplexed output of image data.

Figure 7A:
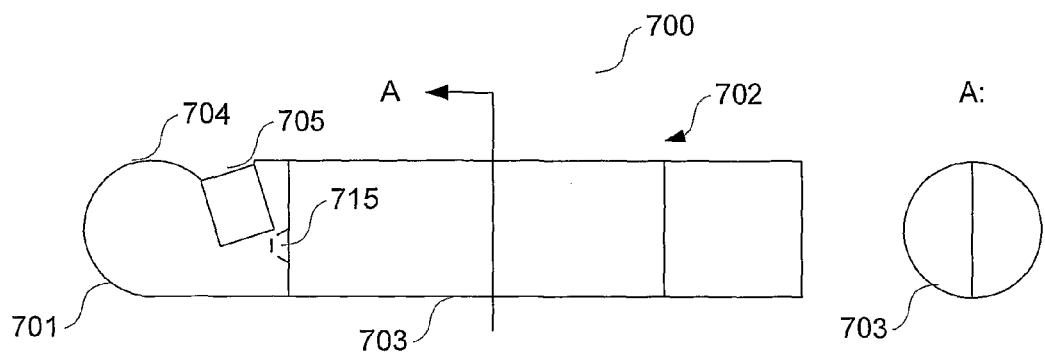
FIGS. 7a-b show a side-view and a top-view of an ultrasound probe with a recess for accommodating a biopsy assembly.
Figure 7B:
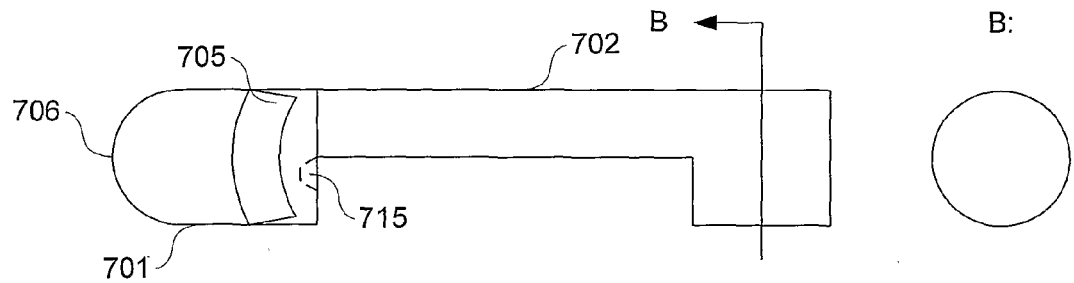

FIGS. 7a-b show a side-view and a top-view of an ultrasound probe with a recess for accommodating a biopsy assembly. In this embodiment, the biopsy assembly comprises the needle guides and is detachable from the ultrasound probe 700. The probe comprises an elongated shaft 702 with a recess 703 and a distal end with a housing 701 configured to accommodate the transducer arrays (not shown). The housing 701 (or scanner head) constitutes a portion of the probe 700. As shown the housing 701 has a cross-section which matches the cross-section of the shaft so as to form a probe with no sharp protrusions. The housing 701 has portions or windows 704,705 behind which the transducer arrays are mounted. The windows are optimized for transmission of ultrasound between the transducers and the medium to be scanned that surrounds the probe during use.

An indentation or notch 715 provides a fixation hole of the assembly.

Figure 7C:
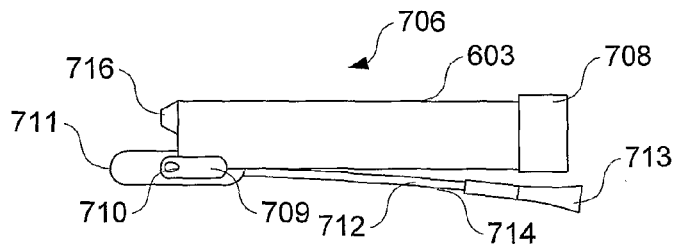
FIG. 7c-d shows a top-view and a side-view of a biopsy assembly.
Figure 7D:
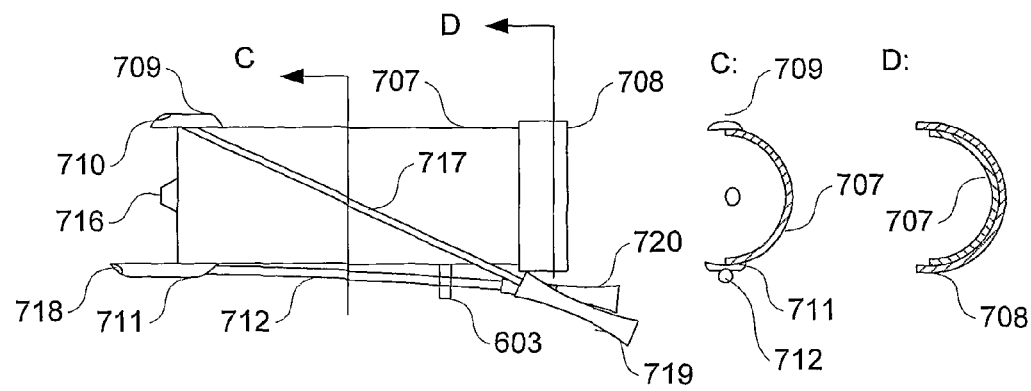

FIGS. 7c-d show a top-view and a side-view of a biopsy assembly. The biopsy assembly 706 comprises the needle guides and is detachable from the ultrasound probe 700.

The biopsy assembly 706 has an elongated member 707 with a cross-section in the shape of a half-section of a tube (e.g. a semi-cylindrical member). This cross-section of the elongated member matches the recess 703 of the probe so as for the assembly to be interconnected with the probe and form an interconnected probe and assembly which is relatively smooth and which is relatively closely interconnected such that larger slits or slots between the probe and assembly are avoided.

A collar 708 provides fixation of the assembly at the handle-end of the probe. At the opposite end of the elongated member a knob or pin 716, when engaging with the notch 715, provides locking of the assembly at the distal end of the probe. Retention is further improved by an upper lip 709 and a lower lip 711 which engage with a portion of the periphery of the probe.

The upper lip 709 and lower lip 711 are configured with openings 710 and 718 wherefrom instruments inserted into the channels 717 and 712 can protract to follow the biopsy paths into the tissue under examination.

The needle guide 712 extends along the periphery of the elongated member 707, but offset from the periphery in a direction away from the point of gravity in a cross-sectional view of the elongated member. This offset distance is only about a few millimetres or a fraction of a millimetre. As shown this offset distance can very along the length of the elongated member 707.

The channels are made from a material that can stand sterilization and is robust to damage caused by a sharp instrument introduced in the guide e.g. high quality stainless steel or a suitable plastic material that can stand autoclaving or for disposable (single use) biopsy guides or assemblies a plastic material that can stand sterilization by gas or radioactive radiation. The channel 712 is held in a fixed position relative to the elongated member by means of a fixture 714.

The elongated member is made from a material that can stand autoclaving.

The channels 717 and 712 terminate at the handle-end in respective end-pieces 719 and 720 which are shaped as a convex cylinder for the operator of the probe to place two fingers and securely (single-handed) maintaining the finger grip when the instrument or needle is to be introduced into the guide. The end-pieces may optionally have a tactile surface on a portion of surface to facilitate secure handling. Preferably, marking on the end-pieces corresponds to marking of the bi-plane images acquired by means of the first transducer in side-fire mode and end-fire mode, respectively, when displayed on a display screen.

Figure 7E:
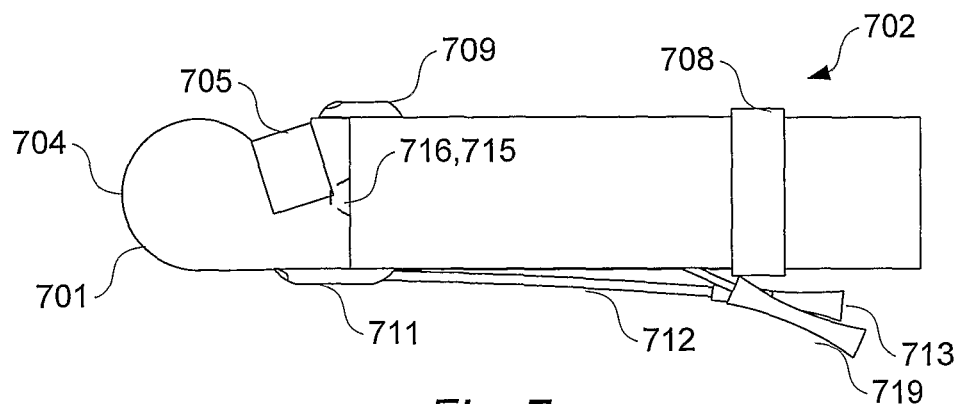
FIG. 7e shows an interconnected ultrasound probe and biopsy assembly.

FIG. 7e shows an interconnected ultrasound probe and biopsy assembly. It can be seen that the collar 708 and upper lip 709 and lower lip 711 engage with the probe. It can further be seen that the knob or pin 716 engages with the notch 715 to form a locking mechanism.

Figure 7F:
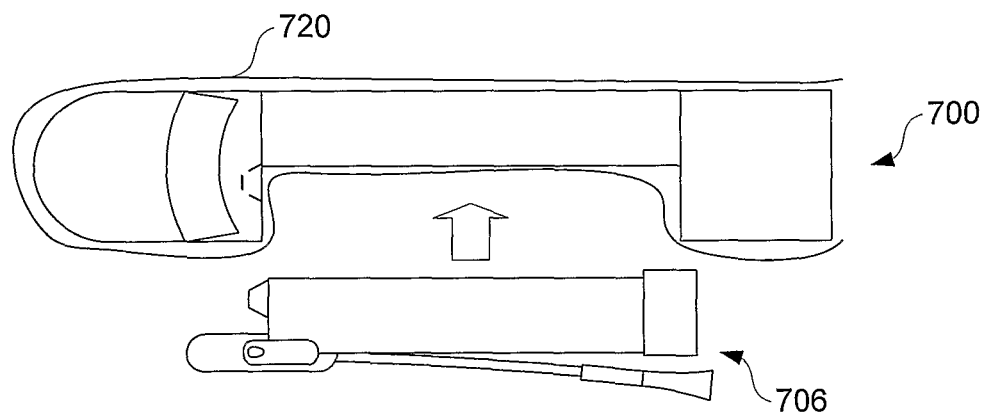
FIG. 7f shows an ultrasound probe protected by a cover.

FIG. 7f shows an ultrasound probe protected by a cover. The assembly is detached from probe, but is shown next to the probe. The probe is covered by a cover 720 such that the probe is protected from direct contact with the patient when introduced into a body cavity. Thereby disinfection of the probe after use is not needed. The probe is ready for its next use after common cleaning thereof (when the cover 720 has been removed). Thereby, the assembly 706 does not need to come into direct contact with the probe. Arranging the assembly in this manner is particularly advantageous in that a needle will not penetrate the cover 720. As a result the probe is not unnecessarily contaminated and thus need not be disinfected after each use.

Figure 7G:
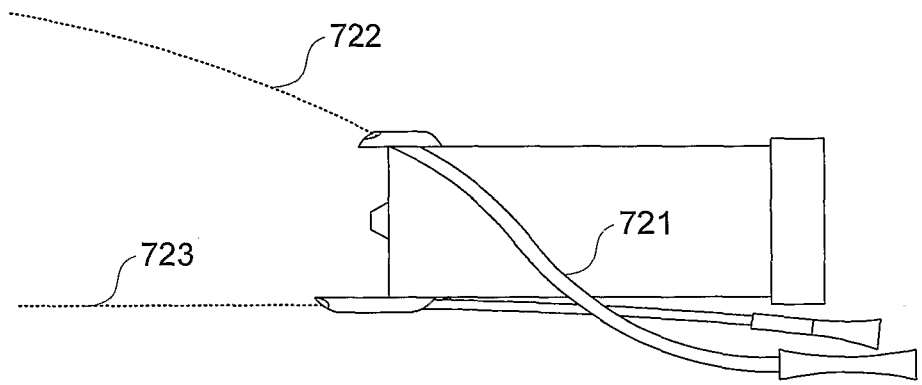
FIG. 7g shows a biopsy assembly with a curved needle guide.

FIG. 7g shows a biopsy assembly with a curved needle guide. In this embodiment the transverse guide 721 is shown as a guide with a curved channel. Thereby, the angle of protraction can be arranged with fewer constraints than a straight channel. Especially, the handle-end of the guide can be placed with fewer constraints thus allowing a more ergonomic or operator friendly design. Reference numerals 722 and 723 designate paths of the needles guided through the transverse and longitudinally extending needle guide, respectively.

Figure 8A:
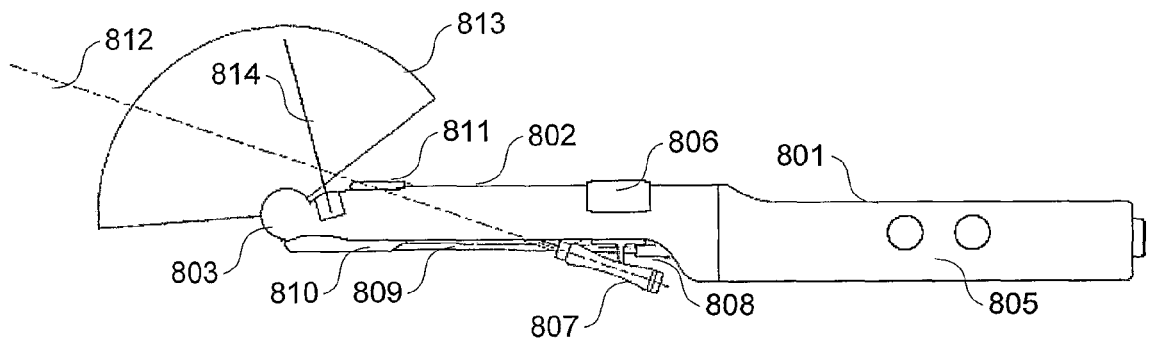
FIGS. 8a and 8b show a side-view and a 3D view of an ultrasound probe in a bi-plane mode.
Figure 8B:
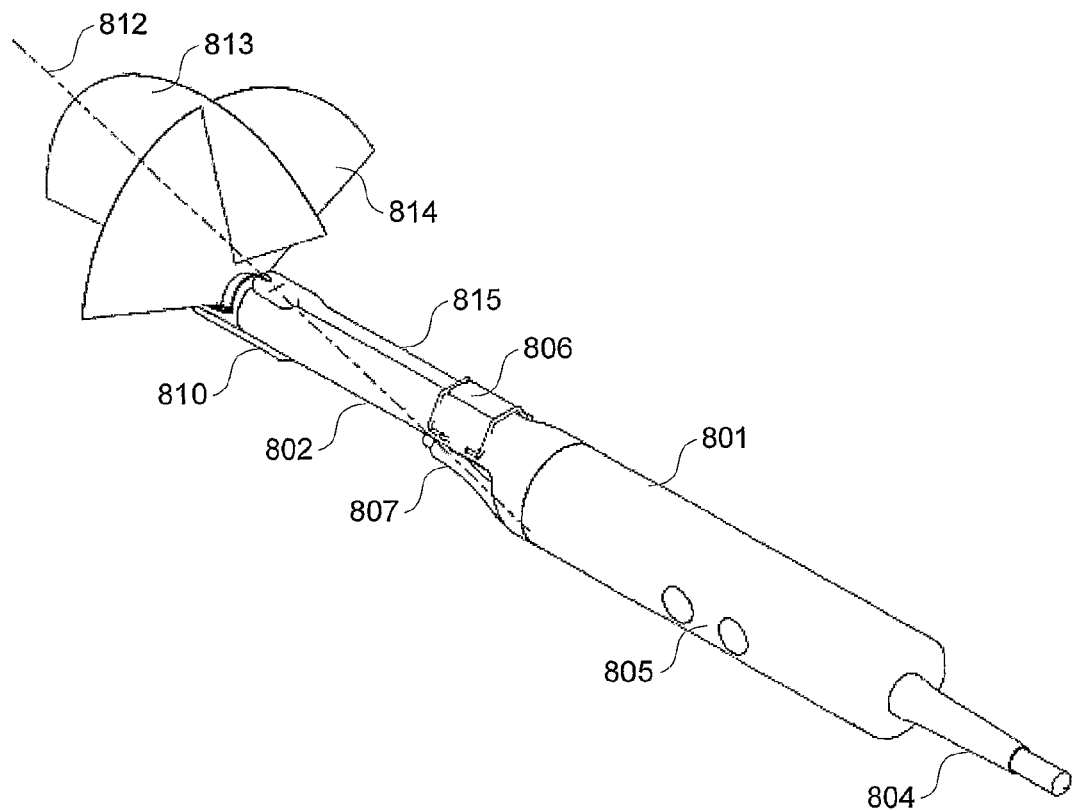

FIGS. 8a and 8b show a side-view and a 3D view of an ultrasound probe in a bi-plane mode. The probe comprises a handle 801 and a shaft 802 with a scanning head 803. The handle has two buttons 805 for shifting between modes of the probe e.g. one of the buttons selects the end-fire mode and the other selects the bi-plane mode. At the handle-end a cable connection 804 is provided.

The probe is interconnected with a biopsy assembly with an elongated member 815 which is maintained interconnected with the probe by means of a clamp 806. An upper lip 811, a lower lip 810, a longitudinal guide channel 809 and end-pieces 808 thereof are also shown. Further, an end-piece 807 of a transverse guide is also shown and the biopsy path 812 established by the transverse guide is also shown.

The probe is shown in a mode that provides bi-plane imaging with a sagittal. field of view 813 and a transverse field of view 814. The sagittal field of view 813 is arranged to provide primarily a side-fire view.

Figure 9A:
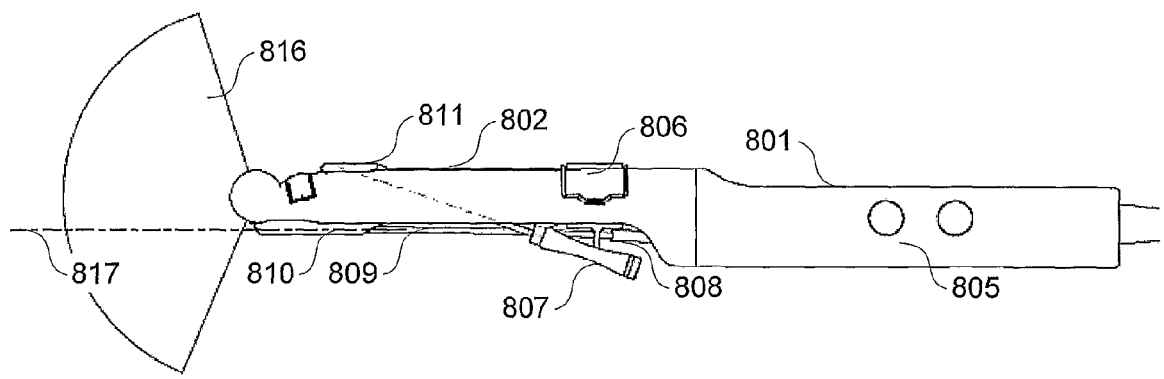
FIGS. 9a and 9b show a side-view and a 3D view of an ultrasound probe in an end-fire mode.
Figure 9B:
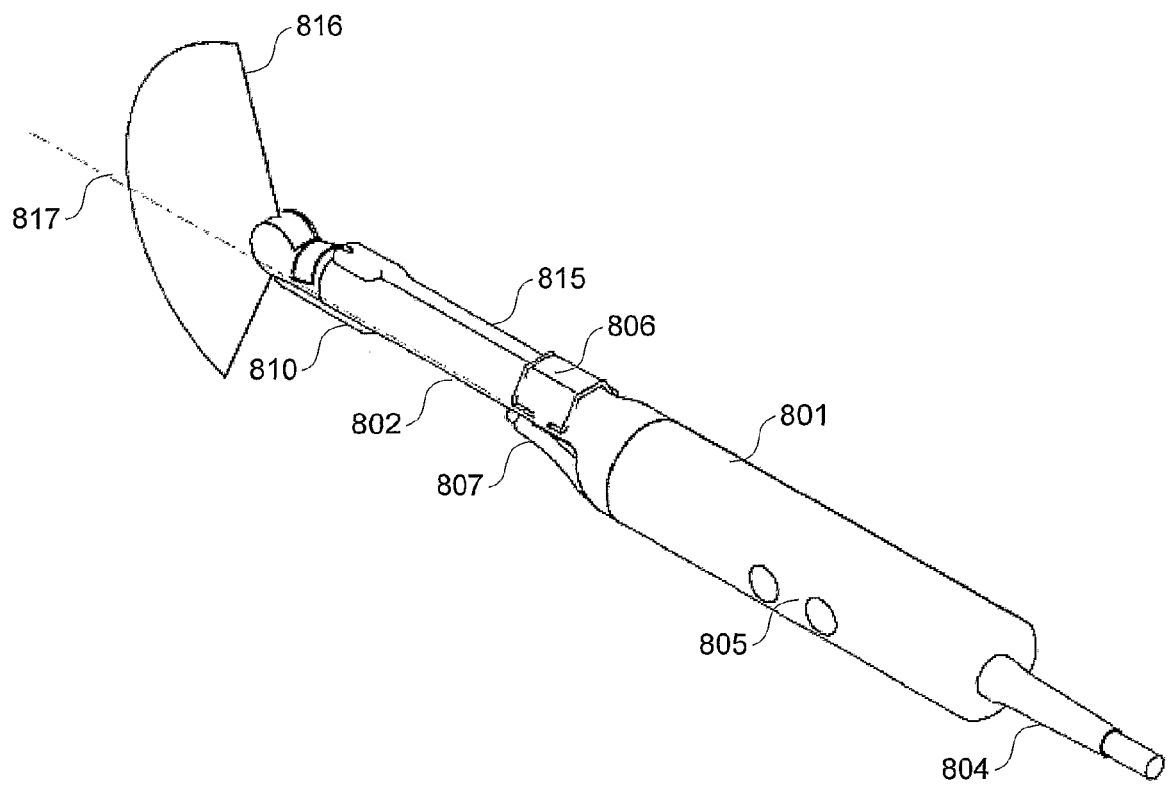

FIGS. 9a and 9b show a side-view and a 3D view of an ultrasound probe in an end-fire mode. The sagiftal field of view 816 is arranged to provide primarily an end-fire view. The biopsy path 817 established by the transverse guide is also shown.

Figure 10A:
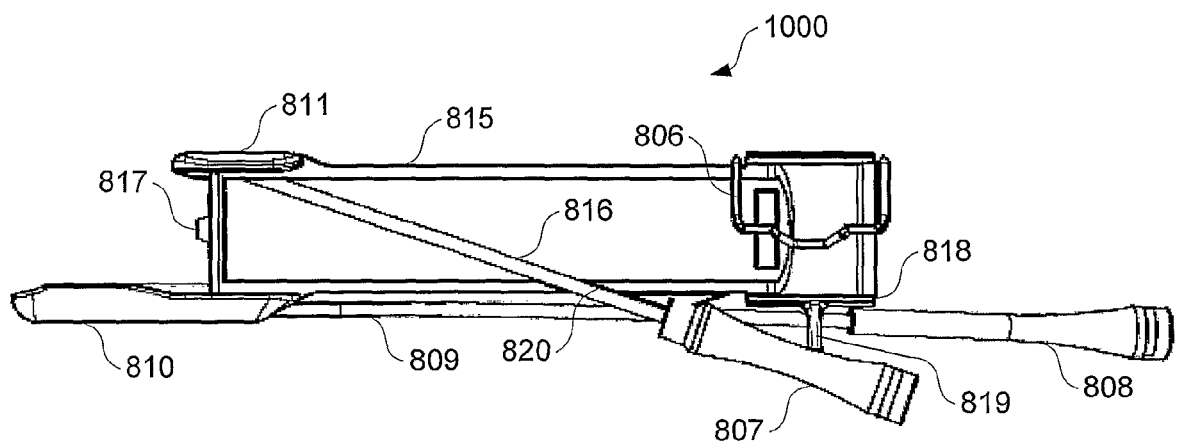
FIGS. 10a and 10b show a side-view and a 3D view of a biopsy assembly.
Figure 10B:
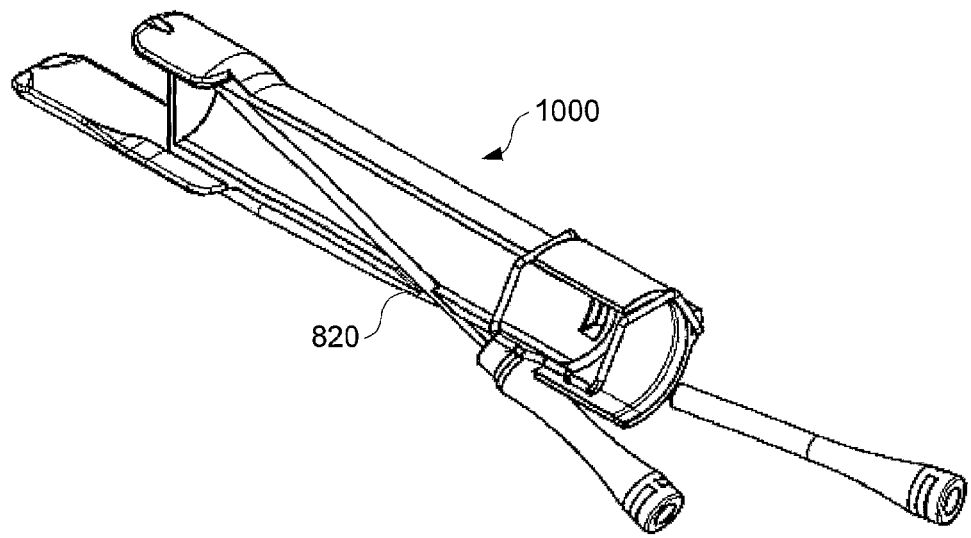

FIGS. 10a and 10b show a side-view and a 3D view of a biopsy assembly. This assembly is the biopsy assembly shown interconnected with the probe on FIGS. 8 and 9, but here shown in greater detail.

The biopsy assembly 1000 has an elongated member 815. A collar 818 provides retention or fixation of the assembly at the handle-end of the probe. At the opposite end of the elongated member a knob or pin 817 provides retention or fixation of the assembly at the distal end of the probe. Retention is further improved by an upper lip 811 and a lower lip 810 which engage with a portion of the periphery of the probe.

The upper lip 811 and lower lip 810 is configured with openings (not shown) wherefrom instruments inserted into the channels 816 and 809 can protract to follow the biopsy paths into the tissue under examination.

The needle guide 809 extends along the periphery of the elongated member 815 and is held in a fixed position in the handle-end by a fixation protrusion 819. The needle guide 816 extends transverse to the longitudinal axis of the elongated member 815 and is held in a fixed position in the handle-end by a duct 820 in the elongated member 815. The duct 820 fixates the guide by friction. At the opposite ends of the guides 816,809, the guides are fixated by the upper lip 811 and lower lip 810.

The channels 816 and 809 terminate at the handle-end in respective end-pieces 807 and 808 which are shaped as a convex cylinder for the operator of the probe to place two fingers and securely (single-handed) maintaining the finger grip when the instrument or needle is to be introduced into the guide. Preferably, marking on the end-pieces correspond to marking of acquired bi-plane images, respectively, when displayed on a display screen. As shown the end-pieces can have a different outer shape e.g. an outer shape as concave cylinder (807) or an outer shape as a combined cylinder and cone.

As stated in the above, the field of view comprises a number of scan lines. The image is focused along these scan lines either by the physical shape of the transducer elements or electronically or by a combination of the two. When using a combination of the two, the elements of the array can have a surface shape which is convex in a direction transverse to the length of the line array and which is substantially straight in a direction longitudinal to the length of the array.

Since the array is curved the transducer elements thereof have surface normals that extend mutually radially from the surfaces of the array elements or at least some of the elements have surface normals that extend mutually radially from the surfaces of the array elements. Please recall that a surface normal to a flat surface is a three-dimensional vector which is perpendicular to that surface. A normal to a non-flat surface at a point on the surface is a vector which is perpendicular to the tangent plane to that surface at the point. The radial surface normals (disregarding their length) of the transducer element can coincide with the scan lines and thus, define the field of view provided by the transducer array.

Although primarily linear curved array embodiments have been described alternative embodiments can comprise curved multi-line arrays (curved matrixes of transducer elements). Still alternative, embodiments can comprise element transducers e.g. single element transducers arranged in mechanically moveable configurations.

The invention claimed is:

1. An ultrasound probe, comprising:
an elongated member with a longitudinal axis and first and second opposing ends, wherein one of the opposing ends includes a circular arc with a depression between the circular arc and the other one of the opposing ends and the depression is contiguous with at least one end of the circular arc, and the depression extends along an axis which is transverse to a direction of the longitudinal axis;
a first transducer array disposed along at least a sub-portion of the circular arc in the direction of the longitudinal axis, where the first transducer array has a first field of view established by acquiring a first image along radial lines in a first image plane, wherein the first image plane extends in a direction along the longitudinal axis projected from the one of the opposing ends, and wherein the first image plane extends from a first side of the circular arc and towards a second side of the circular arc opposing the first side of the circular arc;
a second transducer array disposed in the depression in a direction of the transverse axis, where the second transducer has a second field of view established by acquiring a second image along radial lines in a second image plane, which extends in a transverse direction along the transverse axis relative to the first image plane and the longitudinal axis of the elongated member, and the second transducer array is a separate array relative to the first transducer array; and
wherein the second transducer array is mechanically disposed in an inclined position in the depression at an angle less than 90 degrees with respect to the longitudinal axis and towards the circular arc;

a first needle guide configured to guide a first needle along a path which intersects with the first field of view and the transverse axis; and a second needle guide configured to guide a second needle along a path which intersects with the first field of view, wherein the first needle guide is arranged to guide the first needle in a direction transverse to the longitudinal axis, and where the second needle guide is arranged to guide the second needle in a direction along the elongated member, and wherein the elongated member has a shape that is configured for mechanical interconnection with the probe and to match a recess of the probe so as to provide a combination of the assembly and probe, when interconnected, that can be circumscribed by a cylinder that covers at least a portion of the length of the elongated member and has a diameter that is within the range of 12 to 30 millimeters.

2. The ultrasound probe according to claim 1, where the second image plane intersects the first field of view of the first transducer.

3. The ultrasound probe according to claim 1, where only a sub-portion of the first transducer array is excited to transmit when the first and second transducer arrays are concurrently transmitting.

4. The ultrasound probe according to claim 1, where the first field of view and the second field of view are of a same size.

5. The ultrasound probe according to claim 1, where the first transducer array comprises a curved array shaped to substantially follow an arc segment of a circle with a radius selected from a range of 2 to 20, 4 to 16, 4 to 12, or 4 to 8 millimeters.

6. The ultrasound probe according to claim 1, where the angle is about 73 degrees.

7. The ultrasound probe according to claim 1, where the second image plane extends at an angle that is within a range of 40 to 85 degrees with respect to the longitudinal axis.

8. The ultrasound probe according to claim 1, where the first transducer array is arranged on a more distal portion of the first or second end than the second transducer.

9. The ultrasound probe according to claim 1, where the ultrasound probe is configured to enable selection of: a first mode wherein an end-view image is acquired from a first portion of the first transducer array with a field of view that covers scan lines at each side of the longitudinal axis, and a second mode wherein a side-view image is acquired from a second portion of the first transducer array with a field of view that covers scan lines at each side of the transverse axis.

10. The ultrasound probe according to claim 9, where the first and second portion of the first transducer array has a field of view that covers a first and second sector of scan lines; and where the first and second sector are arranged to cover a common sector of scan lines.

11. The ultrasound probe according to claim 1, where the second image is acquired in a second mode.

12. The ultrasound probe according to claim 1, configured with a multiplexer for a combined parallel and time-multiplexed output of image data.

13. The ultrasound probe transducer according to claim 1, configured with a coupling for interconnection with a biopsy assembly.

14. The ultrasound sound probe according to claim 1, where the first needle guide is arranged to provide an angle between the first needle, when inserted into the needle guide, and the longitudinal axis of the elongated member within the range of 10 to 50 degrees.

15. The ultrasound sound probe according to claim 1, where the needle guides are arranged, with respect to the elongated member, to make the first and second needles, when inserted into the first and second needle guides, protract at opposite positions with respect to a cross-section of the biopsy assembly.

16. The ultrasound sound probe according to claim 1, where the second needle guide extends along a periphery of the elongated member, but offset from the periphery in a direction away from a point of gravity in a cross-sectional view of the elongated member.

17. The ultrasound sound probe according to claim 1, where at least one of the first or first or second needle guides is shaped as a tube with an entry end configured for entry of a needle and an exit end configured for the needle to project from the needle guide.

* * * * *